United States Patent [19]

Ault et al.

[11] Patent Number: 5,493,042

[45] Date of Patent: Feb. 20, 1996

[54] PROCESS FOR REMOVING SILANES FROM BY-PRODUCT STREAM

[75] Inventors: Andrew L. Ault, Union, Ky.; David H. Bramer, Hanover, Ind.; Steven K. Freeburne, Edgewood, Ky.

[73] Assignee: Dow Corning Corporation, Midland, Mich.

[21] Appl. No.: 491,193

[22] Filed: Jun. 15, 1995

[51] Int. Cl.$^6$ .................................................... C07F 7/08
[52] U.S. Cl. .................................................... 556/466
[58] Field of Search ............................................ 556/466

[56] References Cited

U.S. PATENT DOCUMENTS

| | | | |
|---|---|---|---|
| 4,297,500 | 10/1981 | Finke et al. | 556/466 |
| 4,985,579 | 7/1991 | Bokerman et al. | 556/466 |
| 5,292,909 | 3/1994 | Chadwick et al. | 556/466 X |
| 5,292,912 | 3/1994 | Chadwick et al. | 556/466 X |
| 5,302,736 | 4/1994 | Kalchauer et al. | 556/466 X |
| 5,321,147 | 6/1994 | Chadwick et al. | 556/466 |

FOREIGN PATENT DOCUMENTS 89396  8/1956  Czechoslovakia .

OTHER PUBLICATIONS

Sommer et al., J. Org. Chem. 32:2470–2472 (1967).

*Primary Examiner*—Paul F. Shaver
*Attorney, Agent, or Firm*—William F. Boley

[57] ABSTRACT

A process for treating a by-product stream, resulting from the commercial manufacture of methylchlorosilanes, to remove residual silanes where the residual silanes comprise low-boiling hydrosilanes. The process comprises a first step where the by-product stream is contacted with hydrogen chloride in the presence of a chlorination catalyst to convert the low-boiling hydrosilanes to chlorosilanes. In a second step, the modified by-product stream comprising the chlorosilanes is contacted with activated carbon which adsorbs higher-boiling silanes including chlorosilanes, thereby forming a final by-product stream reduced in lower-boiling hydrosilanes and in total silanes. The present process is especially useful for removing silanes from by-product streams intended for incineration, thus reducing silica during combustion of the by-product stream in the incinerator.

17 Claims, No Drawings

5,493,042

PROCESS FOR REMOVING SILANES FROM BY-PRODUCT STREAM

BACKGROUND OF INVENTION

The present invention is a process for treating a by-product stream, resulting from the commercial manufacture of methylchlorosilanes, to remove residual silanes where the residual silanes comprise low-boiling hydrosilanes. The process comprises a first step where the by-product stream is contacted with hydrogen chloride in the presence of a chlorination catalyst to convert the low-boiling hydrosilanes to chlorosilanes. In a second step, the modified by-product stream comprising the chlorosilanes is contacted with activated carbon which adsorbs higher-boiling silanes including chlorosilanes, thereby forming a final by-product stream reduced in lower-boiling hydrosilanes and in total silanes. The present process is especially useful for removing silanes from by-product streams intended for incineration, thus reducing silica during combustion of the by-product stream in the incinerator.

The commercial production of methylchlorosilanes involves the contact of methyl chloride with silicon metalloid in the presence of a catalyst comprising copper at temperatures generally within a range of about 300° C. to 350° C. Typically this process is optimized for the production of dimethyldichlorosilane, with lessor amounts of methylsilanes, methylchlorosilanes, methylhydrosilanes, $C_2$ to $C_5$ hydrocarbons, polysilanes, polysiloxanes, silylmethylenes, and other species being formed. The product mixture can also contain unreacted methyl chloride. This product mixture usually undergoes a series of process steps such as distillation, rearrangement, condensation, and the like, to optimize the recovery of dimethyldichlorosilanes or other desired silanes. A consequence of these production processes is by-product streams. Such by-product streams can result, for example, from the venting or purging of equipment used in making and isolating the methylchlorosilanes. The by-product streams can be highly concentrated in by-products or may be diluted in inert purge gases such as nitrogen.

The present process provides a method where essentially all of the silanes present in such by-product streams can be recovered from the by-product streams. The silanes can then be further processed into useful products. The present process is especially useful for treating by-product streams which are to be incinerated to make them safe for venting to the environment. During the incineration process silanes in the by-product stream can pyrolyze to form particulate silica which can collect in the incinerator creating heat transfer problems and causing plugging. Removal of silanes from the by-product stream by the present process can greatly reduce the formation of particulate silica in an incinerator.

The present inventors have found that activated carbon can adsorb silanes, including chlorosilanes, methylchlorosilanes, methylsilanes, and methylhydrochlorosilanes, from a by-product stream. However, activated carbon is not effective for adsorbing the lower-boiling hydrosilanes such as methylsilane, dimethylsilane, and silane ($SiH_4$), from such by-product streams. Provided herein is a process where the by-product stream is first contacted with hydrogen chloride in the presence of a chlorination catalyst, to chlorinate the low-boiling hydrosilanes converting them to chlorosilanes which are adsorbed by activated carbon. By this process essentially all of the silanes can be recovered from the by-product stream.

Petrov et al., Synthesis of Organosilicon Monomers, Consultants Bureau, NY, N.Y., 1964, p. 416, report that the Si—H bonds of silicon hydrides such as $SiH_4$, $ClSiH_3$, and $CH_3SiH_3$ will react with hydrogen chloride in the presence of $AlCl_3$ to effect chlorination of the silicon hydride.

Sommer et al., J. Org. Chem. 32:2470–2472 (1967), disclose that organosilicon hydrides react with hydrogen halides in the presence of Group VIII metals to form organosilicon halides and halogen. Sommer et al. studied the reaction of $(C_2H_5)_3SiH$ with HCl to produce $(C_2H_5)_3SiCl$.

Bokerman et al., U.S. Pat. No. 4,985,579 describe a process for the removal of hydrogen containing silane impurities from organosilanes with similar boiling points. In the process described by Bokerman et al., the hydrogen containing silane is reacted with a hydrogen halide in the presence of a halogenation catalyst to replace the hydrogen on the silane with a halide and create a modified silane. The substitution of the heavier halide for the hydrogen increases the boiling point of the modified silane to facilitate the separation of the modified silane from organosilanes having a boiling point similar to that of the modified silane prior to halogenation.

Zizka et al., Czech. Pat. No. 89396, published Apr. 15, 1959, describe a process for the recovery of methyl chloride from a gaseous by-product stream containing silanes. Zizka et al. teach treating the by-product stream with dilute NaOH or KOH solution to remove hydrolyzable silanes. The treated gas is then contacted with activated carbon, which adsorbs the methyl chloride. The methyl chloride is recovered from the activated carbon by thermal desorption.

SUMMARY OF INVENTION

The present invention is a process for treating a by-product stream, resulting from the commercial manufacture of methylchlorosilanes, to remove residual silanes where the residual silanes comprise low-boiling hydrosilanes. The process comprises a first step where the by-product stream is contacted with hydrogen chloride in the presence of a chlorination catalyst to convert the low-boiling hydrosilanes to chlorosilanes. In a second step, the modified by-product stream comprising the chlorosilanes is contacted with activated carbon which adsorbs higher-boiling silanes including chlorosilanes, thereby forming a final by-product stream reduced in lower-boiling hydrosilanes and in total silanes. The present process is especially useful for removing silanes from by-product streams intended for incineration, thus reducing silica during combustion of the by-product stream in the incinerator.

DESCRIPTION OF INVENTION

The present invention is a process for treating a by-product stream comprising silanes. The process comprises:

(A) contacting a by-product stream comprising a low-boiling hydrosilane described by formula $Me_xSiH_{4-x}$ were Me is methyl and x=0 to 2 with a least a stoichiometric amount of hydrogen chloride in the presence of a chlorination catalyst thereby forming a modified by-product stream comprising a chlorosilane, (B) contacting the modified by-product stream with activated carbon to adsorb the chlorosilane, and (C) recovering a final by-product stream reduced in low-boiling hydrosilane content.

The by-product stream useful in the present process can be those liquid and gaseous by-product streams associated with commercial processes for the production of methylchlorosilanes. Preferred is when the by-product stream is a gaseous mixture. Such commercial processes can include, for example, the direct process for reacting methyl chloride with silicon metalloid, distillation processes, condensation processes, and redistribution processes. The by-product stream may be the result of leakage, venting, purging or other similar events involving equipment for making and processing methylchlorosilanes.

Compositions of typical by-product streams which are useful in the present process are provided in the examples provided herein. The by-product stream must contain a low-boiling hydrosilane selected from a group described by formula $Me_xSiH_{4-x}$ where Me is methyl and x=0, 1, or 2. The low-boiling hydrosilane can be silane ($SiH_4$), methylsilane ($MeSiH_3$), dimethylsilane ($Me_2SiH_2$) and mixtures thereof. Preferred is when the low-boiling hydrosilane is selected from a group consisting of methylsilane and dimethylsilane and mixtures thereof.

In addition to the low-boiling hydrosilane, the by-product stream may contain higher-boiling hydrosilanes such as trimethylsilane ($Me_3SiH$), methylchlorosilane ($MeH_2SiCl$), dimethylchlorosilane ($Me_2HSiCl$), and methyldichlorosilane ($MeHSiCl_2$). These higher-boiling hydrosilanes can also be chlorinated in the present process increasing their boiling point and facilitating their recovery by a process such as condensation.

The by-product stream can contain tetramethylsilane and methylchlorosilanes i.e. trimethytchlorosilane, dimethyldichlorosilane, and methyltrichlorosilane. The by-product stream can contain methyl chloride, short-chain hydrocarbons, and inert gases such as nitrogen.

The chlorination of hydrosilanes by hydrogen chloride in the presence of a chlorination catalyst is a very fast reaction having a high exotherm. Therefore, to allow good control of the heat in the reactor in which the chlorination process is run it is preferred that the by-product stream comprise less than about one mole percent of total hydrosilanes, including the low-boiling hydrosilanes and higher-boiling hydrosilanes. Even more preferred is when the by-product stream comprises less than about 0.5 mole percent of hydrosilanes. If necessary, the by-product mixture can be diluted with a gas such as nitrogen or with other by-product streams having lessor amounts of hydrosilanes.

It is preferred that the by-product stream comprising the low-boiling hydrosilane be contacted with hydrogen chloride in the presence of a packed-bed of the chlorination catalyst. Feed rate of the by-product stream comprising the low-boiling hydrosilane can be varied within wide limits and is dependent on such factors as the type and concentration of catalyst and the concentration of hydrosilanes in the by-product stream. Guidance as to useful feed rates for the by-product stream is found in the examples herein.

Hydrogen chloride is provided to the present process as a source of chlorine for the chlorination of the hydrosilanes. It is preferred that the hydrogen chloride be provided to the process in at least a stoichiometric amount in relation to total silicon-bonded hydrogen present in the by-product stream. Lessor amounts of hydrogen chloride may be provided to the process, but will result in reduced conversion of methylsilane and dimethylsilane. The maximum amount of hydrogen chloride which can be added to the process is generally only limited by economic considerations.

The present process requires a chlorination catalyst. The chlorination catalyst can be any element or compound thereof capable of facilitating the replacement of a silicon-bonded hydrogen with a chlorine atom. The chlorination catalyst useful in the present process can be selected from a group consisting of palladium, platinum, rhodium, ruthenium, nickel, osmium, iridium, and compounds thereof. A preferred catalyst is selected from a group consisting of palladium, platinum, ruthenium, rhodium, and nickel and compounds of any of these metals. The term "compounds" includes inorganic compounds, for example, metal salts and oxides as well as organometallic compounds.

It is preferred that the metal or metal compound be supported on a solid substrate. The solid substrate can be any inert material of appropriate size and proper affinity for the metal or metal compound, for example, particulate carbon or silica. The preferred substrate is carbon. More preferred is carbon with a surface area of about 1000 $M^2/g$. It is preferred that the metal or metal compound be present on the solid substrate at concentrations from about 0.05 to 10 weight percent. More preferred is when the metal or metal compound is present on the solid substrate at a concentration within a range of about 0.1 to one weight percent. The inventors believe that metal or metal compound concentrations lower than about 0.05 weight percent may facilitate the reaction of hydrosilanes with hydrogen chloride; however, the efficiency of the reaction may be reduced as evidenced by lower conversions and longer residence times. Conversely, metal or metal compound concentrations greater than about 10 weight percent of the support material may be utilized; however, no significant benefit is perceived except in the case of nickel. A useful concentration range for nickel and nickel compounds is about 5 to 15 weight percent of the support material. A preferred concentration of nickel and nickel compounds on the solid support is about 10 weight percent.

Unsupported metals and metal compounds, as described above, can also function as equivalent catalysts in the present process. The unsupported catalyst can be, for example, a finely divided particulate. A useful concentration range for the unsupported catalyst is about 500 to 10,000 ppm. Although higher concentrations of catalyst will work in the process, there is no perceived advantage. Concentrations lower than about 500 ppm of catalyst may work, but with a slower conversion rate.

A preferred chlorination catalyst for use in the present process is palladium supported on carbon. Even more preferred is a chlorination catalyst comprising about 0.1 to one weight percent palladium supported on carbon, based on the combined weight of the palladium and carbon.

The chlorination reaction of the present process is a very fast exothermic reaction that can occur at ambient temperatures and generate large amounts of heat causing the reactor and its content to rise to high temperatures. Therefore, as discussed above, to control the heat within the reactor at safe levels it may be desirable to limit the mole percent of hydrosilanes in the by-product stream. Generally, the chlorination reaction can be run at a temperature within a range of about 30° C. to 1000° C. A preferred temperature is within a range of about 50° C. to 800° C. Most preferred is a temperature within a range of about 200° C. to 500° C.

In step (A) of the present process the low-boiling hydrosilanes are chlorinated forming chlorosilanes. In addition, other higher-boiling hydrosilanes which may be present in the by-product stream are chlorinated. After conduct of chlorination step (A) and before contacting the modified by-product stream comprising the chlorosilanes with activated carbon it is preferred to pass the modified by-product stream through a low-temperature condenser. The low-temperature condenser can be of conventional design used to condense chlorosilanes. By reducing the concentration of chlorosilanes present in the modified by-product stream by condensation, the volume of by-product stream the activated carbon can process before break through of the chlorosilanes occurs can be greatly increased.

The modified by-product stream comprising the chlorosilane, with or without an intervening condensation step, is contacted with activated carbon to adsorb the chlorosilane. The present inventors have found that activated carbon is a good adsorbent for all silanes found in by-product streams as described herein, with the exception of the low-boiling hydrosilanes i.e. methylsilane, dimethylsilane, and silane ($SiH_4$). The present process converts these low-boiling hydrosilanes to chlorosilanes which are readily adsorbed by activated carbon. Therefore, a final by-product steam can be recovered from the present process which is essentially free of silanes including the low-boiling hydrosilanes.

The modified by-product stream is contacted with activated carbon to adsorb the chlorosilanes formed during step (A) as well as any other silanes present in the by-product stream. The physical form of the activated carbon is not critical to the present invention and can be, for example, flakes, chips, pellets, and powder. By "activated carbon" it is meant a microcrystalline, nongraphite form of carbon, having an internal porosity, the carbon having been activated by standard methods known in the art for producing activated carbon, for example, chemical or gas activation as described in Kirk-Othmer, Concise Encyclopedia of Chemical Technology, John Wiley & Sons publishers, 1985, p. 204–205. The activated carbon can be, for example, a bituminous coal-based activated carbon or a coconut shell-based activated carbon. The preferred activated carbon is a bituminous coal-based activated carbon.

In a preferred process the modified by-product steam is contacted with one or more packed-beds of the activated carbon operated in a temperature swing adsorption (TSA) mode. For example, the modified by-product stream can be passed through a first packed-bed of activated carbon until the activated carbon is nearly saturated with silanes, the modified by-product stream flow can then be diverted to a second packed-bed of activated carbon. The silanes can then be recovered from the nearly saturated bed of activated carbon by heating the bed to a temperature causing desorption of the silanes from the activated carbon and passing an inert sweep gas such as nitrogen through the activated carbon bed. A preferred temperature for effecting desorption of the silanes is above about 180° C. Even more preferred is a temperature within a range of about 200° C. to 250° C. The modified by-product stream flow can then be switched between the activated carbon beds while allowing for the activated carbon beds to be alternated between an adsorption and desorption mode, thereby providing for a continuous process.

A final by-product stream reduced in low-boiling hydrosilane content is recovered. By "recovered it is meant that a final by-product stream reduced in low-boiling hydrosilane content is separated from the activated carbon. The recovery can be effected, for example, by passing the by-product stream through a packed-bed of activated carbon.

The final by-product stream reduced in chlorosilane content can be further treated by a process such as incineration. The incinerator may function as an energy recovery unit having positioned therein heat exchange elements. The reduction of silanes in the final by-product stream reduces the amount of pyrogenic silica formed during the incineration process which can deposit in the incinerator reducing heat transfer efficiency.

The following examples are provided to illustrate the present invention. These examples are not intended to limit the scope of the present claims.

Example 1. A series of runs were made to evaluate the effects of gas velocity on chlorination of hydrosilanes in the presence of a palladium supported on carbon catalyst.

The reactor comprised a 1.3 cm internal diameter stainless steel tube packed with approximately a 38 cm column of 0.1 weight percent palladium supported on carbon catalyst (Englehard Corporation, Iselin, N.J.). The reactor was non-insulated and non-heated. For each run, a gaseous by-product stream of an average composition as described in Table 1 was fed to the top of the reactor at the gas velocity (Gas Vel.) reported in Table 2. Hydrogen chloride was fed to the reactor at 100 percent stoichiometric excess in relation to silicon-bonded hydrogen present in the gaseous mixture. The internal temperature of the reactor was monitored by means of a thermal couple and the maximum temperature reached for each run is reported in Table 2 (Final Temp.). The effluent from the reactor was analyzed by gas chromatography using a flame ionization detector (GC-FID). The percent reduction of total silicon-hydrogen bonds (% Si—H Conv.) and the percent reduction of $MeSiH_3$ plus $Me_2SiH_2$ ($MeSiH_3 + Me_2SiH_2$ Conv.) in the by-product stream is reported in Table 2.

TABLE 1

| By-Product Stream Composition | |
|---|---|
| Component | Weight Percent |
| $N_2$ | 1 |
| $SiH_4$ | 2 |
| $CH_4$ | 2 |
| $MeSiH_3$ | 15 |
| $Me_2SiH_2$ | 34 |
| $i\text{-}C_4H_{10}$ | 4 |
| MeCl | 4 |
| $n\text{-}C_4H_{10}$ | 2 |
| $Me_3SiH$ | 1 |
| $MeH_2SiCl$ | 7 |
| $Me_3SiH$ | 8 |
| $i\text{-}C_5H_{14}$ | 14 |
| $Me_2HSiCl$ | 5 |
| $MeHSiCl_2$ | 2 |
| $Me_2SiCl_2$ | 1 |

TABLE 2

Effect of By-Product Stream Gas Velocity on Si—H Conversion and Reactor Temperature

| Run No. | Gas Vel. (cm/s) | Final Temp. (°C.) | Si—H Conv. (%) | $MeSiH_3$ + $Me_2SiH_2$ Conv. (%) |
|---|---|---|---|---|
| 1 | 1.5 | 35 | 43 | >99 |
| 2 | 7.6 | 68 | 66 | 97 |
| 4 | 9.1 | 95 | 69 | 98 |
| 5 | 26.5 | 47 | 46 | 72 |

Example 2. A series of runs were made to evaluate the effect of pre-heating of the reactor on chlorination of hydrosilanes in the presence of a palladium supported on carbon catalyst.

The runs were made in a reactor containing a palladium supported on carbon catalyst similar to that described in Example 1. For this series of runs the reactor was insulated. The reactor was pre-heated to the temperature described in Table 3. A gaseous by-product stream of the composition described in Table 1 was fed to the pre-heated reactor at a rate of 26.5 cm/s. Hydrogen chloride was fed to the reactor at 100 percent stoichiometric excess in relation to silicon-bonded hydrogen present in the gaseous mixture. The internal temperature of the reactor was monitored as described in Example 1 and is reported in Table 3. The effluent from the reactor was analyzed by GC-FID. The percent reduction of total silicon-hydrogen bonds (% Si—H Conv.) and the percent reduction of $MeSiH_3$ plus $Me_2SiH_2$ ($MeSiH_3$+$Me_2SiH_2$ Conv.) in the by-product mixture is reported in Table 3.

TABLE 3

Effect of Pre-Heating of Reactor On Si—H Conversion

| Run No. | Pre-Heat (°C.) | Final Temp. (°C.) | Si—H Conv. (%) | $MeSiH_3$ + $Me_2SiH_2$ Conv. (%) |
|---|---|---|---|---|
| 6 | 90 | 420 | 100 | 100 |
| 7 | — | 165 | 64 | 96 |
| 9 | 50 | 580 | 88 | 99 |
| 10 | — | 415 | 81 | 98 |

Example 3. Effect of hydrogen chloride concentration on initiation of reaction for chlorination of hydrosilanes at ambient temperature in the presence of a palladium supported on carbon catalyst was evaluated. The reactor and palladium supported on carbon catalyst used for this run were similar to that reported in Example 1. A by-product stream similar in composition to that reported in Table 4 was fed to the reactor at a gas velocity of 46 cm/s. Initially, hydrogen chloride gas was fed to the reactor at a concentration slightly less than stoichiometric (in relation to the silicon-bonded hydrogen). No reaction as assessed by the lack of a temperature rise in the reactor was observed. Hydrogen chloride gas was then fed to the reactor at 10 percent stoichiometric excess and no temperature rise occurred. The hydrogen chloride feed was increased to 100 stoichiometric excess. The temperature of the reactor increased slowly from 34° C. to 52° C. over a 30 minute period. A sample of the reactor effluent was taken at this time and analyzed by GC-FID and showed essentially no reduction in silicon-bonded hydrogen in the effluent. Approximately five minutes later the temperature of the reactor started to increase rapidly, peaking at 163° C. in 15 minutes and then decreasing to 149° C. A sample of the effluent from the reactor was taken after the reactor temperature peaked and analyzed by GC-FID. The sample had a 93 percent reduction in total silicon-bonded hydrogen and a 100 percent reduction in $Me_2SiH_2$ and $MeH_2SiCl$.

Example 4. The ability of a bituminous coal-based activated carbon to adsorb silanes in a temperature swing adsorption (TSA) process was assessed. A packed bed of activated carbon approximately 2.5 meters in height was formed in a two inch inside diameter carbon-steel column. The activated carbon was 4×10 mesh bituminous coal-based activated carbon (Calgon, Pittsburgh, Pa.). A by-product stream of a composition similar to that described in Table 4 was fed to the column at a rate of 3 cm/s. Adsorption was effected at room temperature. Effluent from the column was monitored by GC-FID. Essentially, all of the $Me_4Si$, $Me_3SiH$, $Me_2HSiCl$, $MeHSiCl_2$, $Me_3SiCl$, $MeSiCl_2$ and $Me_2SiCl_2$ was adsorbed from the by-product stream until break through occurred. The hydrosilanes $MeSiH_3$ and $Me_2SiH_2$ were only minimally adsorbed by the activated carbon. After break through occurred the activated carbon bed was desorbed by heating to a temperature of 175° C. and passing nitrogen gas through the bed. The effluent from the desorption process was recovered by condensation and weighed. The adsorption/desorption process was repeated for a total of seven cycles with minimal change in the ability of the activated carbon to adsorb silanes. The average capacity of the activated carbon to adsorb compounds from the by-product gas was determined to be 0.32 g per gram of activated carbon.

TABLE 4

By-Product Stream Composition

| Component | Weight Percent |
|---|---|
| $N_2$ | 55.6 |
| $CH_4$ | 3.7 |
| $SiH_4$ | 0.4 |
| $MeSiH_3$ | 3.1 |
| MeCl | 3.5 |
| $Me_2SiH_2$ | 3.6 |
| $Me_3SiH$ | 0.1 |
| $MeH_2SiCl$ | 1.6 |
| $Me_4Si$ | 1.3 |
| $HSiCl_3$ | 0.6 |
| $Me_2HSiCl$ | 4.0 |
| $MeHSiCl_2$ | 8.0 |
| $Me_3SiCl$ | 2.8 |
| $MeSiCl_3$ | 2.7 |
| $Me_2SiCl_2$ | 5.1 |
| $C_2$–$C_5$ Hydrocarbons | 3.7 |

Example 5. The ability of a coconut shell-based activated carbon to adsorb silanes in a temperature swing adsorption process was assessed. The activated carbon was a 6×8 mesh coconut shell-based carbon (Chemical Design Inc., Lockport, N.Y.). A packed bed of the activated carbon was formed similar to that described in Example 4. A by-product stream of a composition similar to that described in Example 4 was fed to the column at a rate of 3 cm/s. Adsorption was effected at room temperature. Effluent from the column was monitored by GC-FID. Essentially, all of the $Me_4Si$, $Me_3SiH$, $Me_2HSiCl$, $MeHSiCl_2$, $Me_3SiCl$, $MeSiCl_2$, and $Me_2SiCl_2$ was adsorbed from the by-product stream until break through occurred. The hydrosilanes $MeSiH_3$ and $Me_2SiH_2$ were only minimally adsorbed onto the activated carbon. After break though occurred the activated carbon bed was desorbed by heating to a temperature of 175° C. and passing nitrogen gas through the bed. The effluent from the desorption process was recovered by condensation and weighed. The adsorption/desorption process was repeated for a total of ten cycles with minimal change in the ability of the activated carbon to adsorb silanes. The average capacity of the coconut shell based activated carbon to adsorb compounds from the by-product stream was determined to be 0.26 g per gram of activated carbon.

We claim:

1. A process for treating a by-product stream comprising silanes, the process comprising:

(A) contacting a by-product stream comprising a low-boiling hydrosilane described by formula $Me_xSiH_{4-x}$ were Me is methyl and x=0 to 2 with at least a stoichiometric amount of hydrogen chloride in the presence of a chlorination catalyst thereby forming a modified by-product stream comprising chlorosilane, (B) contacting the modified by-product stream with activated carbon to adsorb the chlorosilane, and (C) recovering a final by-product stream reduced in low-boiling hydrosilane content.

2. A process according to claim 1, where the by-product steam is a gaseous mixture.

3. A process according to claim 1, where the by-product stream comprises less than about 0.5 mole percent of total hydrosilanes.

4. A process according to claim 1, where the by-product stream is contacted with a packed-bed of the chlorination catalyst.

5. A process according to claim 1, where the low-boiling hydrosilane is selected from a group consisting of methylsilane and dimethylsilane.

6. A process according to claim 1, where the chlorination catalyst is selected from a group consisting of palladium, platinum, rhodium, ruthenium, nickel, osmium, iridium, and compounds thereof.

7. A process according to claim 1, where the chlorination catalyst is selected from a group consisting of palladium, platinum, ruthenium, rhodium, nickel, and compounds thereof.

8. A process according to claim 6, where the chlorination catalyst is supported on a solid substrate.

9. A process according to claim 8, where the solid substrate is carbon and the chlorination catalyst comprises about 0.05 to 10 weight percent of the combined weight of substrate and catalyst.

10. A process according to claim 7, where the chlorination catalyst is supported on a solid substrate.

11. A process according to claim 10, were the solid substrate is carbon and the chlorination catalyst comprises about 0.05 to 10 weight percent of the combined weight of substrate and catalyst.

12. A process according to claim 1, where the chlorination catalyst comprises about 0.1 to one weight percent palladium supported on carbon, based on the combined weight of the palladium and carbon.

13. A process according to claim 1, where the by-product stream is contacted with the chlorination catalyst at a temperature within a range of about 200° C. to 500° C.

14. A process according to claim 1, where the activated carbon is bituminous coal-based.

15. A process according to claim 1, where the chlorosilane is desorbed from the activated carbon at a temperature within a range of about 200° C. to 250° C. and the desorbed activated carbon is contacted with additional modified by-product stream.

16. A process according to claim 1, where the final by-product stream reduced in low-boiling hydrosilane content is incinerated.

17. A process for treating a by-product stream comprising silanes, the process comprising:

(A) contacting a by-product stream comprising a low-boiling hydrosilane selected from a group consisting of methylsilane and dimethylsilane with at least a stoichiometric amount of hydrogen chloride in the presence of a chlorination catalyst comprising palladium supported on carbon, thereby forming a modified by-product stream comprising chlorosilane, (B) condensing the modified by-product stream comprising the chlorosilane thereby forming a condensible fraction and a non-condensible fraction comprising chlorosilane, (C) contacting the non-condensible fraction with activated carbon to adsorb the chlorosilane, thereby providing a final by-product stream reduced in chlorosilane, and (D) incinerating the final by-product stream.

* * * * *